US006867035B2

(12) United States Patent
Ong

(10) Patent No.: US 6,867,035 B2
(45) Date of Patent: Mar. 15, 2005

(54) CELL LIBRARIES INDEXED TO NUCLEIC ACID MICROARRAYS

(75) Inventor: Christopher J. Ong, Vancouver (CA)

(73) Assignee: The University of British Columbia, Vancouver (CA)

(*) Notice: Subject to any disclaimer, the term of this patent is extended or adjusted under 35 U.S.C. 154(b) by 372 days.

(21) Appl. No.: 09/883,745

(22) Filed: Jun. 18, 2001

(65) Prior Publication Data

US 2001/0053524 A1 Dec. 20, 2001

(30) Foreign Application Priority Data

Jun. 16, 2000 (CA) .............................. 2309371

(51) Int. Cl.$^7$ ........................ C12M 1/34; C12Q 1/68; C12P 19/34; C07H 21/02; C07H 21/04
(52) U.S. Cl. ..................... 435/287.2; 435/6; 435/91.1; 435/91.2; 435/91.51; 435/287.1
(58) Field of Search ....................... 435/6, 91.1, 91.2, 435/183, 91.51, 283.1, 287.1, 287.2; 436/94, 501; 536/23.1, 24.3, 24.33, 25.3, 25.32

(56) References Cited

U.S. PATENT DOCUMENTS

| | | | |
|---|---|---|---|
| 6,077,673 A | 6/2000 | Chenchick | |
| 6,136,566 A | 10/2000 | Sands | |
| 6,207,371 B1 | 3/2001 | Zambrowicz | |
| 6,436,707 B1 * | 8/2002 | Zambrowicz et al. | ........ 435/455 |

FOREIGN PATENT DOCUMENTS

| | | | |
|---|---|---|---|
| GB | 1295951 A1 * | 3/2003 | |
| WO | WO 98/14614 A | 4/1998 | |
| WO | WO 99/02719 | 1/1999 | |
| WO | WO 01/57251 | 8/2001 | |

OTHER PUBLICATIONS

Kelly et al., DNA microarray analyses of genes regulated during the differentiation of embryonic stem cells. Molecular Reproduction and development, 56, 113–123, Jun. 2000.*
Baker et al., Developmental Biology(1997), 185:201–214.
Botwell, Nature Genetics Supplement(1999) 21:25–32.
Brown and Nolan, Human Molecular Genetics(1998), 7(10):1627–1633.
Chan and Evans, Trends in Genetics(1991), 7(3):76.
Kuwano, Zoological Science(1996), 13:277–83.
Skarnes et al., Genes & Development(1992), 6(6):903–918.
Southern et al., Nature Genetics Supplement(1999) 21:5–9.
Udy and Evans, BioTechniques(1994), 17(5):887–894.
Ure et al. Trends in Genetics(1992), 8(1):6.
Wiles et al., Nature Genetics(2000), 24:13–14.
Wurst et al., Genetics(1995), 139:889–899.
Zambrowicz, Nature(1998), 392(6676):608–611.
Zambrowicz, B. and Friedrich, G., "Comprehensive mammalian genetics; history and future prospects of gene trapping in the mouse," 1988, Int. J. Dev. Biol. 42: 1025–1036.
Chen, H., et al., "A chromosome 18–specific gene array based on trapped exons: Implications for bipolar disorder," 2000, Abstract (program #1427) from 50$^{th}$ Annual Meeting of the American Society for Human Genetics (Philadelphia, PA. –Oct. 3–7, 2000).
Skarnes, W., "The identification of new genes: gene trapping in transgenic mice," 1993, Current Opinion in Biotechnology 4:684–689.
Evans, M.J., et al., "Gene trapping and functional genomics," 1997, Trends in Genetics 13(9): 370–374.
Shoemaker, DD., et al., "Experimental annotation of the human genome using microarray technology," 2001, Nature, 409(6822):922–927.
Penn, S., et al., "Mining the human genome using Microarrays of open reading frames," 2000 Nature Genetics 26(3):315–318.
Hicks et al., Nature Genetics (1997), 16:338–344.

* cited by examiner

Primary Examiner—Ethan Whisenant
Assistant Examiner—Frank Lu
(74) Attorney, Agent, or Firm—Ann W. Speckman

(57) ABSTRACT

This invention provides a method for selecting a clone of an ES cell containing a mutation in a gene that is expressed in a test cell comprising: (a) providing cDNA obtained by reverse transcription of mRNA of the test cell; (b) providing a collection of cultured ES cells organized into individual clones, wherein each clone is of an ES cell having a mutation in an exon in its genome, the mutation being in a different exon in cells of different clones; (c) providing an array of different single stranded polynucleotides, the polynucleotides being fragments of exons containing mutations in (b); (d) exposing the cDNA to the array under conditions permitting hybridization of polynucleotides in the array to nucleic acids; (e) detecting hybridization of cDNA to a polynucleotide on the array; and, (f) selecting a clone in the collection from which a hybridizing polynucleotide detected at (c) is an exon fragment. This invention also provides a system for testing expression of a gene in a test cell. Also provided is a preferred exon trap vector for mutating ES cells.

9 Claims, No Drawings

CELL LIBRARIES INDEXED TO NUCLEIC ACID MICROARRAYS

CROSS-REFERENCE TO RELATED APPLICATION

Applicant claims foreign priority benefits, under 35 U.S.C. §119(a), of Canadian Application, Ser. No. 2,309,371, filed Jun. 16, 2000.

FIELD OF THE INVENTION

This invention relates to libraries of embryonic stem cells in which the genome of members of the library are modified by gene trapping.

BACKGROUND

Genome-wide mutagenesis in lower organisms (e.g. bacteria, nematodes, yeast, zebra fish and Drosophila) followed by screening or selection for mutants using phenotypic assays has proven to be a useful methodology for revealing gene function in these organisms.

The mouse provides a very useful mammalian animal model for studying gene function. The mouse model possesses significant advantages because of its evolutionary relatedness to humans, similarity to humans with respect to the development of complex tissues and organs, and because it provides opportunity to rapidly identify homologous genes through regions of genomic sestina. Large-scale mutagenesis in programs using mice now play a significant role in the study of mammalian gene function (Brown & Nolan (1998) Human Molecular Genetics, 7:1627–1633). The mutagen of choice for use in large-scale mouse studies is N-ethyl-N-nitrosourea (ENU) which is administered to male mice.

Technological advances in culture and maintenance of embryonic stem (ES) cells has provided new opportunities for study of eukaryotic genomes including that of the mouse. Murine ES cells are derived from the inner cell mass of about a 3.5 day embryo or blastocyst and can be maintained in an undifferentiated, pluripotent state in culture. ES cells can be genetically manipulated in vitro and these cells may subsequently be introduced into an embryo by blastocyst microinjection or embryo aggregation techniques. Upon reintroduction into the embryo, ES cells can contribute to the formation of all tissues of the resulting chimeric organism. ES cell contribution to germ cells of the reproductive organs results in germline transmission of mutations introduced into the ES cell genome. For these reasons, mutation of ES cells is used as another means for generating mutations in the mouse genome. For example, murine ES cells may be irradiated (Brown & Nolan [supra]) or mutated through the use of insertional mutagenesis such as transposon tagging, retroviral integration, or gene trap mutagenesis.

Screening strategies in mouse mutagenesis programs vary according to phenotype under study and according to the means by which mutations are produced. For example, various expression based strategies are described for screening cell lines or animals derived from ES cells in which a gene trap vector has been used to generate a mutation (e.g. Baker, et al. (1997) Dev. Biol., 185:201–14; Kuwano, R. (1996) Zool. Sci., 13:277–83; Wurst, et al. (1995) Genetics, 139:889–99; and PCT application published Jan. 21, 1999 under WO 99/02719). While the above-described methodologies which make use of large-scale mutagenesis are used for study of the murine genome, gene sequence based systems have also been developed and are concurrently used for analysis of the mouse genome. The latter approach is expected to be used in parallel with mutagenic approaches to provide an enlarged catalogue of mouse mutations and phenotypes for gene function studies (Brown & Nolan [supra]).

The current gene sequence based strategy of choice for the mouse makes use of the production of a library of ES gene trap clones indexed by either polynucleotide fragments derived from regions flanking the site of gene trap integration or by DNA sequence information derived from such fragments. The premise behind this approach is that most mammalian genes will soon be characterized from sequences of "expressed sequence tags" (ESTs). An example of such an ES cell library is known as Omnibank™ and is described, for example by Brown & Nolan [supra], Zambrowicz, et al. (1998) Nature, 392:608–611, and in U.S. Pat. Nos. 6,136,566 and 6,207,371. Another example is described in Wiles, M. V. et al. (2000) Nature Genetics, 24:13–14. Such libraries may be generated by introducing an exon trap vector into ES cells and cloning separate cell lines representing individual trap vector integration events. The exon trap vector described by Zambrowicz, et al. (e.g. construct VICTR 20) comprises an upstream mutagenic cassette containing a splice acceptor (SA) sequence fused to a selectable reporter gene followed by a polyadnylation (polyA) sequence. This portion of the vector interrupts expression of the endogenous gene. A downstream portion of the trap vector ensures that integration of the trap into an exon may be detected without transcription of the endogenous gene. This downstream portion contains a promoter functional in the ES cell, linked to a reporter gene followed by a splice donor (SD) sequence. The promoter drives expression of the reporter gene together with endogenous DNA downstream to an endogenous polyA site. Sequence tags from endogenous (trapped) genes may be readily recovered using 3' RACE-PCR, which generates polynucleotides corresponding to the regions which flank the site of integration of the vector. Furthermore, disruption of the endogenous gene by an exon trap vector permits one to readily generate transgenic and "knock-out" mice which are heterozygous for the mutation or are entirely deficient in the trapped gene function. This is accomplished using the ES cell methodologies described above. Chimeric animals that are generated by this procedure may be bred to provide homologous mutants. Further information regarding the construction and use of exon trap vectors, amplification of flanking regions, and generation of chimeric animals is found in WO 99/02719.

SUMMARY OF THE INVENTION

This invention results from the inventor recognizing that mutant ES cell libraries such as Omnibank™ are not used to their full potential because these libraries are addressed, searched, or otherwise accessed through use of known or predetermined sequence information or probes. As is described in U.S. Pat. Nos. 6,136,566 and 6,207,371, such a library works by indexing representative samples of mutant ES cell clones to polynucleotide fragments derived from the exon of the mutant cell into which the trap vector has become integrated. Actual fragments may be stored in some fashion and made available for hybridization studies against pre-designed or selected oligonucleotide probes, or the fragments are represented in a sequence database. In the case of a database, the indexing system of the library is addressed by searching the database for sequences similar to a preselected target sequence. In either case, the end result is the identification of a fragment (or fragment sequence) which is indexed (associated) to a particular ES cell clone. The particular clone may then be made available for further study, including for generation of mice mutated at the site of the fragment in the mouse genome.

This invention is based on the inventor also recognizing that a mutant ES cell library as described above need not be addressed, searched, or otherwise accessed using known sequences or pre-selected probes. Rather, the library may be addressed as part of a screening method, with the result being that indexed ES cell clones are identified as being relevant to the screen, without the user having any pre-existing knowledge or assumptions about the underlying genes involved. Regardless, the user has immediate access to genes that are relevant to the screen and immediate access to sequence information associated with the gene.

The inventor recognizes that in order to use an ES cell library to its full potential in a screening methodology, it is necessary that the methodology function on a scale commensurate with the size of the library. This requires that the screening assay be unlike a traditional phenotypic or expression screens used in analysis of the results of mutagenesis programs. It is possible to make full use of an ES cell library directly in a screening method by employing nucleic acid microarrays to address the library indexing system and to act as an interface with test samples. Nucleic acid microarrays permit the testing of complex nucleic acid samples for hybridization against literally thousands of polynucleotide fragments simultaneously.

By combining the use of nucleic acid microarrays with current ES cell library methodologies, it is now possible to address the address indexing of such a library by interaction with a complex nucleic acid sample. By addressing the library, it is meant that an association is made between a single hybridization event on the microarray and a corresponding member of the library. The corresponding member of the library is, or is representative of, a sample of the very ES cell clone in which the fragment on the microarray to which hybridization occurs is derived, and in which a mutation exists at the location of the fragment in the genome of an ES cell in the library.

This invention may be used for screening samples representative of a particular biological condition (such as a disease state or stage of cellular differentiation) and comparison may be made to samples taken from cells having different biological conditions or states. The difference in hybridization patterns on nucleic acid microarrays as between the two biological conditions may be readily correlated to the members of the ES cell library used to generate the nucleic acid microarray. The user then has immediate access to ES cell clones in which genes that are differentially affected are tagged by insertion mutagenesis and are also available for sequencing or generation of knock-out organisms.

Accordingly, this invention provides a method for selecting a clone of an ES cell containing a mutation in a gene that is expressed in a test cell comprising:

(a) providing cDNA obtained by reverse transcription of mRNA of the test cell;

(b) providing a collection of cultured ES cells organized into individual clones, wherein each clone is of an ES cell having a mutation in an exon of its genome, the mutation being in a different exon in cells of different clones;

(c) providing an array of different single stranded polynucleotides, the polynucleotides being fragments of the exons containing mutations in (b);

(d) exposing the cDNA to the array under conditions permitting hybridization of polynucleotides in the array to nucleic acids;

(e) detecting hybridization of a polynucleotide on the array; and, (f) selecting a clone in the collection from which a hybridizing polynucleotide detected at (e) is an exon fragment.

This invention also includes a method for comparing gene expression between test cells, comprising:

(a) providing at least two cDNA samples, each sample obtained by reverse transcription of mRNA of a different test cell;

(b) providing a collection of cultured ES cells organized into individual clones, wherein each clone is of an ES cell having a mutation in an exon of its genome, the mutation being in a different exon in cells of different clones;

(c) providing at least one array of different single stranded polynucleotides, the polynucleotides being fragments of the exons containing mutations in (b);

(d) exposing the cDNA samples to the at least one array under conditions permitting hybridization of polynucleotides in the array to nucleic acids;

(e) detecting hybridization of polynucleotides in the at least one array resulting from exposure to the cDNA samples;

(f) selecting clones in the collection from which hybridizing polynucleotides detected at (e) are exon fragments; and, (g) comparing a clone or clones which comprise exon fragments that hybridize to one of the cDNA samples to a clone or clones which comprise exon fragments that hybridize to another of the cDNA samples.

This invention also provides a system for testing expression of a gene in a test cell, comprising:

(a) a collection of cultured ES cells organized into individual clones, wherein each clone is of an ES cell having a mutation in an exon of its genome, the mutation being in a different exon in cells of different clones; and, (b) an array comprising at least 500 different single stranded polynucleotides on a solid support surface, the polynucleotides being fragments of the exons containing mutations in (a).

This invention provides a system comprising the combination of a collection of cultured cells and at least one nucleic acid microarray comprising an array of polynucleotides, wherein the collection and the array are as described above. This combination may additionally comprise a recorded index, which is a record of the association of individual clones in the collection to the position or positions in the array that coincide with polynucleotides derived from the individual clone. This recorded index may be a database stored on a computer-readable medium. Such a recorded index may also comprise information associated with the clone or the derived polynucleotides such as sequence information. The combination may additionally comprise a computer-readable medium which comprises instructions for executing a computer implemented method for searching a database comprising the recorded index; for providing a record of a pattern of hybridization on an array; or, for providing a statistical analysis of such a pattern. An output from such a method for statistical analysis may be coupled to the recorded index (e.g. through the searching method) so as to associate an analysis of a hybridization pattern with information concerning associated clones.

In this invention, "selecting" a clone or clones may be limited to selecting data in a database, which data is representative of a clone or clones of ES cells, or the method may include locating such a clone or clones in a physical collection of cells organized into clones. "Selecting" may also include physically segregating cells of a clone so located. Since many genes may be expressed in a test cell and many polynucleotides may be present on the array, these methods may involve simultaneous hybridization of multiple oligonucleotides to cDNA, thereby permitting multiple clones to be "selected" in the method of this invention. "Selecting" a clone or clones may additionally comprise producing an organism from a cell present in a selected clone. The animal may be heterozygous or homozygous for the mutation in the clone.

"Comparing clones" of this invention may include comparing data pertaining to individual clones as described above, or such "comparing" may be a comparison of phenotypes of cells of the clones or phenotypes of organisms derived from cells of the clones.

In this invention, collections of cultured cells comprising mutations are preferably produced using exon trapping methodologies such as those known in the art and exemplified below. To facilitate production of knock-out organisms from the cultured ES cells, the gene trapping vector should be one which interrupts expression of the exon into which the vector integrates. To facilitate production of the array, the vector should be capable of being a primer target for PCR amplification. Preferably the trap vector will include a reporter driven by a promoter that is functional in the ES cells.

The array used in this invention is preferably a nucleic acid microarray as is known in the art. Such microarrays contain a large plurality of polynucleotide spots stably associated with a solid support surface. Preferably, different polynucleotides used in a single array are not capable of cross-hybridization. However, multiple spots each containing the same or complementary polynucleotides may be present. Typical polynucleotide lengths range from about 120 to about 1000 nucleotides. Spot density may in some cases be as high as $1,000/cm^2$ with the number of spots in a single array being at least 500, preferably at least about 1,000, and in some cases being up to the order of 30,000. Materials and methods for the production and use of such microarrays are well known. A description of the construction of a large-scale microarray containing unique polynucleotides corresponding to individual mouse genes is disclosed in U.S. Pat. No. 6,077,673.

Methods for detection of hybridization events in microarrays are also well known. Typically, hybridization is detected through use of some form of label, all or a component of which is typically placed on nucleic acids in a sample to be exposed to the array. Examples of such labels are fluorescent or radioactive compounds that are typically joined to or incorporated into the cDNA. High-throughput methods and apparatus are available for detecting, recording, and analyzing patterns of labelling resulting from hybridization on these arrays.

Test cells for use in this invention may be any cell for which some aspect of the expression of the cell's genome is to be determined or assessed. Ideally, the test cell will be of the same animal type as the ES cells in the cell collection (library) although the this invention could use test cells from the organism different than that from which the library is derived.

This invention is useful for comparison of differences in gene expression between different test cells. In such an embodiment, one such test cell may be considered a standard for comparison to one or more other test cells of interest. Other test cells may be representative of different biological states or phenotypes. For example, test cells may be representative of different states of differentiation, disease, neoplastic progression, etc.

Methods for obtaining cDNA from the mRNA pool of test cells are well known, as are methods for labelling such cDNA to facilitate detection of hybridization of such cDNA to polynucleotides on a microarray.

ES cells used in this invention may be from any eukaryotic organism from which such cells may be obtained and cultured. Mammals for which ES cells may be obtained and cultured include rodents (e.g. mice and rats), pigs, and humans. However, this invention does not include the generation of humans from ES cells.

The present invention may also include the facilitation of cloning of RACE-PCR products by incorporation of a small selectable sequence between the specific primer sequence used for RACE-PCR and an unpaired splice site on the gene trap vector, such that the small selectable marker is incorporated within the RACE-PCR product which facilitates its cloning.

Accordingly, this invention provides an exon trap vector which is a preferable vector for use in generating mutant ES cells for use in this invention. The vector comprises in a 5' to 3' direction:

(a) an unpaired splice acceptor;
(b) a region encoding a reporter;
(c) one or more polyadenylation signals;
(d) a promoter functional in an ES cell;
(e) a segment encoding a second reporter under transcriptional control of promoter; and,
(f) an unpaired splice donor, wherein the construct additionally comprises a selectable region of 300 base pairs or less between (a) and (b) or between (e) and (f). The selectable region may encode a selectable marker (such as supF) or the selectable region is a recombination site such as att, lox, or frt. Preferably, the selectable region will be immediately adjacent to the sequence in the vector that has been designed or selected to be a primer target for PCR.

DETAILED DESCRIPTION OF PREFERRED EMBODIMENTS OF THE INVENTION

This invention includes indexing a library of genetically altered cells and screening and isolating a particular clone of interest from the library using high-throughput DNA microarrays. The library is used as a source for identifying and obtaining specifically mutated cells, cell lines derived from the individually mutated cells, and cells for use in the production of transgenic non-human animals. This methodology provides an efficient and rapid method for the identification of novel genes, rapid determination of its chromosomal map position and placement of genes on the physical map for the generation of gene transcript maps for eukaryotic genomes and simultaneous generation of gene knock-out organisms for in vivo gene function analyses of corresponding genes. This approach allows the expansion of the scope of biological investigation from studying single genes/proteins to studying all genes/proteins simultaneously.

The present invention encompasses an integrated functional genomics strategy that combines large-scale gene trap mutagenesis and tagging of gene transcripts in ES cells with the high-throughput and versatile nucleic acid microarray technology for genome-wide expression analysis. The method involves the use of DNA microarrays comprising signature DNA fragments corresponding to trapped genes in each embryonic stem cell gene rap clone and screening for identification of differentially regulated trapped genes. The microarrays are indexed to corresponding clones.

Gene trapping may be performed in mice using a gene trap DNA construct comprising two functional units. The first functional segment consists of a mutagenic, detectable component that comprises an unpaired splice acceptor sequence fused to an internal ribosomal entry sequence (IRES) linked to a (e.g. β-galactosidase) reporter gene followed by a polyadenylation signal sequence (e.g. SA-IRES-βgal-pA). The second functional unit encodes a selectable sequence acquisition module consisting of a promoter such as mouse phosphoglycerate kinase-1 (PGK) that is actively transcribed in ES cells, fused to a reporter (e.g. the puromycin N-acetyltransferase gene) followed by an unpaired synthetic consensus splice donor sequence (e.g. PGKpuroSD). A preferred vector comprises one or more small selectable sequences less than 300 bp in length that facilitate cloning of trapped genes by 5' or 3' RACE-PCR. The DNA construct may be the unpaired splice acceptor sequence upstream of a small selectable sequence linked to the primer target sequence used for 5' RACE-PCR. Alternatively, the DNA construct may have the unpaired splice donor sequence downstream of the primer target used for 3' RACE-PCR linked to a small selectable sequence. Such small selectable sequences of less than 300 bp include bacterial selectable markers such as supF or site-specific recombination sites such as attB, loxP or frt.

Transfection of the gene trap DNA construct via electroporation into ES cells results in random integration (the majority of which are single copy vector integration events) into the ES cell genome by illegitimate recombination. The selectable (e.g. PGKpuroSD) gene cassette lacks a polyadenylation signal sequence. Therefore, puromycin resistance from the exemplified vector can only be achieved by splicing into downstream exons and polyadenylation signal sequence of the trapped endogenous gene. The trap vector not only introduces a molecular tag that permits subsequent cloning and identification, chromosomal localization and placement onto the physical map of the trapped gene, but also simultaneously generates ES cells bearing mutations in the respective genes that facilitates generation of knock-out mice.

Each ES cell trap clone obtained simultaneously provides access to the following key pieces of information: 1) partial cDNA gene fragments corresponding to the trapped genes can be cloned by rapid amplification of cDNA ends (3' RACE-PCR); 2) the identity of the novel genes trapped can be determined by obtaining partial gene sequence information through high-throughput DNA sequencing of RACE-PCR products; 3) the chromosomal localization of the trapped genes can be identified by fluorescence in situ hybridization (FISH) mapping; 4) the genomic DNA sequence flanking the site of integration can be rapidly cloned and sequenced providing sequence information that will allow for rapid placement of genes on DNA contigs or the physical map; 5) the direct histochemical demonstration of the pattern of gene expression (e.g. due to the presence of the LacZ reporter gene) in either chimeras or germline animals produced with ES cells can be attained; and, 6) in vivo gene function information can be obtained from phenotypic, physiologic, and biochemical analyses of ES cell-derived knock-out mice and cell lines.

A partial or complete set of randomly genetically altered cells is generated. For example, a library of ES cell gene trap clones is generated by random insertional mutagenesis using the above-described gene trap vector. Each trapped gene is cloned by 3' RACE-PCR. PCR products are then used for the fabrication of DNA microarrays. Quantitative gene expression analyses using DNA microarray hybridization is subsequently performed in order to identify differentially expressed genes in a variety of model systems. Gene chip hybridization probes derived from test and control cell or tissue samples are prepared from defined biological systems, for example: neurodegenerative disease; DNA repair; prostate cancer; adhesion signalling; macrophage activation; immune tolerance and activation; apoptosis; dendritic cell function; and, liver regeneration. An advantage of using the method of this invention prior to DNA sequencing is that sequencing may then be restricted to differentially regulated genes. This represents a huge economical saving.

Significant cross-regulation of certain gene classes in multiple biological systems is anticipated. For example, genes that are up-regulated in apoptosis, neurodegenerative disease, and T-cell anergy may be conversely down-modulated in cancer progression, liver regeneration, T-cell activation, etc. Examination of so many diverse genes gives a perspective on all the processes that simultaneously occur within a model system. The comparison of gene expression profiles between model systems will provide new insight into the role of genes in the context of multiple processes. Therefore, this invention will be useful to identify gene families that play common and unique functional roles in multiple pathways and systems.

PCR products from corresponding differentially regulated trapped genes identified by microarray hybridization are used as DNA templates for sequencing. ES gene trap are subsequently may be selected for chromosomal localization by FISH mapping. Flanking genomic DNA sequence are cloned and subsequently sequenced. Bioinformatic analyses of partial gene sequence information and chromosomal localization is then performed. By comparison of gene sequence and chromosomal position with databases, information with respect to whether the trapped genes are novel or known, are part of a gene family, contain known functions domains, etc. is then determined. Based on the results of bioinformatics, specific ES cell clones are for generation of knock-out mice and determination of in vivo gene expression pattern. Homozygous mutant mice and cell lines are then used for phenotypic, biochemical, and physiologic analyses. Subsequent cycles of gene identification may be performed using hybridization probes derived from mutant mice and cell lines for further rounds of microarray hybridization studies.

Generation of ES Cell Gene Trap Clones

In the following example, gene trap mutagenesis is performed in J1 ES cells. The J1 ES cell line was chosen for the following reasons: 1) J1 cells are derived from a 129 substrain that has been chosen as the source of genomic DNA for the international mouse genome sequencing project; and 2) J1 ES cells were originally derived from an inbred homozygous genotype allowing for easy back-crossing to generate knock-out in inbred background also allows for gene knock-out to be out-crossed onto outbred background with a minimal number of matings.

Gene trapping in ES cells is performed using the gene trap DNA construct described above comprising a mutagenic, detectable component (SA-IRES-βgal-pA) and a selectable sequence acquisition module (PGKpuroSD). Most gene trap events containing SA-βgal-pA result in a null allele (Zambrowicz, et al. [supra], Skarnes, et al. (1991) Genes Dev., 6(6):903–918). Moreover, the expression of the reporter βgal genes is under the control of the endogenous promoter. The pattern of LacZ activity, therefore, mimics that of the endogenous gene allowing for histological assessment of in vivo gene expression pattern. The internal ribosomal entry sequence (IRES) allows for reporter gene translation independently of the reading frame of the splice junction. The PGKpuroSD component of the GST vector results in expression of the puromycin resistance gene as fusion transcripts with the 3' end containing downstream exons and the polyadenylation signal of tagged genes. This fusion transcript allows for the identification of the trapped genes by 3' RACE-PCR in undifferentiated ES cells, even if the genes are not expressed in ES cells.

In order to facilitate cloning of the RACE-PCR fragments, the Gateway™ cloning system by Gibco BRL can be adapted to the PCR strategy of this invention by introducing a 25 bp sequence corresponding to the attB1 site just upstream of the splice donor or splice acceptor sequence and downstream of the gene trap vector specific primers used for RACE-PCR amplification. The attB2 site is incorporated into the adaptor primer. Cloning of the RACE-PCR fragments as described below may then be facilitated by use of the Gateway™ selection systems. Alternatively, a supF gene may be introduced between the gene trap vector specific primer and the splice acceptor or donor site such that upon RACE-PCR amplification the supF sequence is incorporated into the PCR product. Subsequent cloning of RACE-PCR products can then be efficiently performed by selection into P3 plasmid containing *E. coli* such as MC1061/P3. P3 carries an amber AmpR and an amber TetR gene.

Host cells are transformed by any of the well known methods, selected as being suitable for the particular cell type. Electroporation or calcium phosphate mediated transfection are suitable for mammalian cells. A preferred method known for ES cells is electroporation.

A library of gene trap ES cell clones each harbouring mutations in unique genes are generated using the gene trap DNA vector. Each ES cell clone has variable cell numbers and growth rates per well after colony isolation. In order to normalize the ES cell numbers per well after clone isolation, ES cells are trypsinized and split into two plates after a few days of culture. One plate is used to determine cell number using an MTT based assay that is detected using an ELISA plate reader. The ELISA Microplate Autoreader El311™ is employed. Using Bioworks™ software, discontinuous samples are split by merely supplying a file containing cell number data in a comma-delimited format which is easily be exported from Excel™. ES cell clones at varying concentrations in the source plate are individually replated by the automated Biomek 2000™ resulting in consolidation of clones having similar concentrations in the destination 96 well plates. After a few days of culture, three replica 96 well plates are generated using the Biomek 2000™ workstation. Two replica plates of ES cells are cryo-preserved using an improved 96-well plate freezing protocol for ES cells that allows long-term storage (Udy and Evans, (1994) Biotechniques, 17(5):887–94; Ure, et al. (1992) Trends in Genetics, 8(1):6; Chan and Evans, (1991) Trends in Genetics, 7(3):76). All plates are barcoded with unique identifiers.

A third replica plate of cells are used for isolation of total polyA mRNA as templates for reverse transcription (RT) and 3'RACE-PCR (3' rapid amplification of cDNA ends-polymerase chain reaction) RNA from ES clones is isolated using a rapid, automated magnetic bead-based mRNA isolation procedure. The Dynal mRNA Direct™ protocol is automated using a Beckman Biomek 2000™ robotic workstation that is adapted with a magnetic plate (Dynal XS-96T) placed on the work surface of the robotic workstation. The 96-well plates containing ES cell clones are processed automatically on the workstation. Automated RNA extraction is linked with thermocycling by integration of a PTC-200-MJResearch™ thermocycler (with a robotic lid) adjacent to the Biomek 2000™ workstation. The Bioworks™ software program is capable of automated control set-up and activation of the RT and 3' RACE-PCR reactions using universal primers in the thermocycler. After the PCR run, PCR products are transferred directly for PCR purification using the magnetic bead based procedure called solid-phase reversible immobilization (SPRI) of the Whitehead Institute for Genomics Research.

Purified 3' RACE-PCR DNA fragments are then used in preparation of high density DNA microarrays.

Preparation of DNA Microarrays

DNA microarray technology is generally performed on two main types of solid substrates: glass microarrays containing as many as 30,000 DNA spots and nylon membranes containing as many as 5,000 DNA spots. Glass slides have several advantages as described (Southern, et al., (1999) Nat. Gen. Suppl., 21:5–9): 1) target DNA is coupled covalently onto treated glass surface; 2) glass can withstand high temperature and high ionic wash solutions and is non-porous so hybridization volumes can be kept to a minimum which enhances the kinetics of hybridization; 3) glass has virtually no auto fluorescence and very low non specific probe binding which allows very low signals to be quantitated; and, 4) two or more probes can be labelled with different fluorochromes and hybridized together to detect differential hybridization.

There are two mechanical aspects of microarray technology: array spotters (robots) and array scanners such as those described in Bowtell, (1999) Nat. Gen. Suppl., 21:25–32. DNA array spotters are available that have the capacity to spot up to 44,000 spots per standard slide (20 mm×50 mm). The SDDC-1™ DNA arrayer by Engineering Services Inc., (Toronto, Ontario) is suitable for the production of DNA arrays on glass slides.

Microarrays are prepared by spotting PCR derived DNA products each representing a single gene integration or tag event as described above. The first stage involves the spotting of 10,000 DNA targets onto a 20 mm×20 mm area. Target DNA will be prepared and stored in master microtitre plates as described above. Positive controls to be spotted may include 15 housekeeping genes, plasmid DNA, genomic DNA, and 40 spots of GFP DNA.

RACE-PCR DNA libraries in 96 well format may be used for printing microarrays by direct spotting onto glass slides. Microarrays may be prepared by spotting PCR derived DNA products each representing a single gene trap event as described above.

Printing, hybridization, scanning and analyses of microarrays may be performed using the Total Array System™ manufactured by BioRobotics as well as the Virtex™ microarray scanner after co-hybridization of fluorescently labelled probes. The primary expression array data is analyzed using principle component analyses and clustering analyses software programs using the commercially available software programs for image analyses and data extraction such as ImaGene™ by BioDiscovery, ImageQuant™ by Molecular Dynamics and AtlasImage™ by Clontech and using other publicly available software programs such as the Cluster Analyses™ software program from Stanford Genomics Resources and the ArrayView™ software from the NIH National Human Genome Research Institute.

Preparation of cDNA Test Samples and Exposure to Array

The Cy3 and Cy5 fluorescent labels have good incorporation efficiencies with reverse transcriptase, photostability and yield, and are widely separated in their excitation and emission spectra, allowing highly discriminating optical filtration. Alternatively, analyses may be performed using $^{33}$P-labelled cDNA.

Single stranded cDNA probes may be synthesized from 5 μg of total RNA using reverse transcriptase in reactions containing oligo d(T) primers, deoxynucleotides and either Cy3-dUTP or Cy5-dUTP. Prior to labeling, the RNA population will be spiked with 1 μg of GFP RNA produced by in vitro transcription of a plasmid clone with a T3/T7 RNA polymerase initiation signal. This internal control serves to normalize labelling efficiency between RNA preps, to confirm grid location, and measure uniformity of hybridization across the array. Following reverse transcription, RNA will be degraded by treatment with alkali and heat, and fluorescently labelled cDNA purified using Qiagen™ DNA purification columns.

Equivalent amounts of labelled cDNA probes will be combined and exposed to the microarray under a glass cover slip at 65° C. for 8 hours. Slides will be washed under known high stringency conditions, dried, and scanned for fluorescence.

The microarrays may be scanned for fluorescence using the Molecular Dynamics Avalanche™ scanner with lasers specific for the fluorescence of these probes.

DNA Sequencing Component

The tagged genes that display changes in expression in different disease states may be sequenced using an Applied Biosystems™ model 373XL automated laser sequencer.

FISH Mapping for Determining Chromosomal Location

Fluorescence in situ hybridization (FISH) involves labelling a cosmid, phage, plasmid or BAC/PAC clone with a non-isotopic tag, such as biotin or digoxigenin 9 and the labelled probe is then hybridized to metaphase spreads and the fluorescent signals are detected at the site of hybridization to homologous sequences at one chromosome band location.

A universal probe consisting of the approximately 10 kb Gene Sequence Tag DNA vector is used for mapping experiments of all GST integration events in ES clones identified. The use of a universal probe allows efficient sample throughput. The probes are labelled with biotin-14-dUTP or digoxigenin (DIG)-14-dUTP by nick translation. Duplicate slides are run for each probe. On average, it takes 2–4 FISH laboratory experiments to obtain signals adequate to complete the mapping using 4',6-Diamidin-2-phenylindol-dihydrochloride (DAPI) banding. Since characteristics of universal probe hybridization to ES cell chromosomal DNA is optimized, the determination of chromosomal localization by FISH is more efficient and high-throughput. The chromosome position may be confirmed by cytogeneticists. Images may be captured as TIFF files, converted to JPEG format, and subsequently analysed.

Database

The data gathered from the DNA sequencing and FISH treatment of the ES cell gene tag clones may be compiled in a database.

Gene Knock-out Chimeric Mouse Generation

Gene knock-out chimeric mice may be generated from targeted ES cell clones. Weekly microinjections of one to two different ES cell clones into blastocysts for the production of chimeric mice will be performed (approximately 4 and 6 chimeric mice typically will be produced per ES cell clone). Chimeric mice are maintained until germline transmission is achieved, then subjected to further breeding for generation of homozygous mutations, and for specific phenotypic analysis.

Microarray Analyses Example

The Shionogi carcinoma closely mimics the response of human prostate cancer to androgen withdrawal therapy and is a good mouse tumour model system for studying progression to androgen independence. Approximately $5 \times 10^6$ of the parent, androgen dependent Shionogi tumour cells were injected subcutaneously into individual male mice of the DDS strain and the tumours were allowed to grow for about 17–20 days attaining a weight of ~3 g. The host animals were then castrated and subsequently sacrificed 1 day, 2 days, 4 days, and after tumour recurrence. Recurrent, androgen independent tumours (with a mass of ~1 g) are seen between 20–30 days after castration. At each time point, total RNA is extracted from the regressing and recurrent tumours and reverse-transcribed to produce fluorescently labelled-cDNA for hybridization with gene trap microarrays as described above. Changes in gene expression in Shionogi tumours on 290 genes corresponding to ES gene trap clones following castration at days 1, 2, and 4 post castration and in androgen independent tumours were analyzed using the TreeView™ hierarchical clustering software program (M. Eisen, Lawrence Berkely National Laboratory), which identified a cluster of genes that is highly induced following castration and is subsequently down-regulated with progression to androgen independence.

Although the foregoing invention has been described in some detail by way of illustration and example for purposes of clarity of understanding, it will be readily apparent to those of skill in the art in light of the teachings of this invention that changes and modification may be made thereto without departing from the spirit or scope of the appended claims. All patents, patent applications and publications referred to herein are hereby incorporated by reference.

What is claimed is:

1. A method for selecting a clone of an ES cell containing a mutation in a gene that is expressed in a test cell comprising:

(a) providing cDNA obtained by reverse transcription of mRNA of the test cell;

(b) providing a collection of cultured ES cells organized into individual clones, wherein each clone is of an ES cell having a mutation in an exon in its genome, the mutation being in a different exon in cells of different clones;

(c) providing an array of different single stranded polynucleotides, the polynucleotides being fragments of exons containing mutations in (b);

(d) exposing the cDNA to the array under conditions permitting hybridization of polynucleotides in the array to nucleic acids;

(e) detecting hybridization of cDNA to a polynucleotide on the array; and, (f) selecting a clone in the collection from which a hybridizing polynucleotide detected at (c) is an exon fragment.

2. The method of claim 1, wherein the ES cells are murine.

3. The method of claim 1, wherein mutations in the ES cells are as a result of introducing an exon trap vector into ES cells.

4. The method of claim 1, wherein the array is a nucleic acid microarray.

5. The method of claim 4, wherein the microarray comprises at least 500 different polynucleotides on a solid support surface.

6. The method of claim 5, wherein the microarray comprises at least about 1,000 different polynucleotides.

7. The method of claim 1, wherein the cDNA is labelled to facilitate detection at (e).

8. The method of claim 7, wherein the label is fluorescent or radioactive.

9. The method of claim 1, wherein selecting a clone comprises physically segregating a sample of ES cells from a selected clone.

* * * * *